(12) United States Patent
Papp

(10) Patent No.: US 8,690,822 B2
(45) Date of Patent: *Apr. 8, 2014

(54) DRUG DELIVERY MEDICAL DEVICES

(75) Inventor: John Papp, Temecula, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/347,611

(22) Filed: Jan. 10, 2012

(65) Prior Publication Data

US 2012/0116304 A1    May 10, 2012

Related U.S. Application Data

(63) Continuation of application No. 11/821,998, filed on Jun. 25, 2007, now Pat. No. 8,109,904.

(51) Int. Cl.
*A61M 37/00* (2006.01)
*A61M 31/00* (2006.01)
*A61M 29/00* (2006.01)

(52) U.S. Cl.
USPC .............. 604/103.01; 604/97.01; 604/103.05; 604/103.06

(58) Field of Classification Search
USPC .................. 604/96.01–97.03, 99.04, 100.01, 604/103.01, 103.05, 103.06, 103.08, 103.11
See application file for complete search history.

(56) References Cited

U.S. PATENT DOCUMENTS

| | | |
|---|---|---|
| 5,196,024 A | 3/1993 | Barath |
| 5,320,634 A | 6/1994 | Vigil et al. |
| 5,681,281 A | 10/1997 | Vigil et al. |
| 6,334,856 B1 | 1/2002 | Allen et al. |
| 6,503,231 B1 | 1/2003 | Prausnitz et al. |
| 6,611,707 B1 | 8/2003 | Prausnitz et al. |
| 6,743,211 B1 | 6/2004 | Prausnitz et al. |
| 6,808,518 B2 | 10/2004 | Wellman et al. |
| 6,991,617 B2 | 1/2006 | Hektner et al. |
| 7,413,558 B2 | 8/2008 | Kelley et al. |
| 7,569,032 B2 | 8/2009 | Naimark et al. |
| 7,611,484 B2 | 11/2009 | Wellman et al. |
| 7,972,351 B2 | 7/2011 | Trinidad |
| 8,034,066 B2 | 10/2011 | Goeken et al. |
| 8,043,259 B2 | 10/2011 | Radisch et al. |
| 2001/0020151 A1 | 9/2001 | Reed et al. |
| 2003/0065303 A1 | 4/2003 | Wellman et al. |
| 2003/0163148 A1 | 8/2003 | Wang et al. |
| 2004/0044308 A1 | 3/2004 | Naimark et al. |
| 2004/0064093 A1* | 4/2004 | Hektner et al. .......... 604/103.01 |
| 2004/0133223 A1 | 7/2004 | Weber |
| 2004/0204677 A1 | 10/2004 | Wellman et al. |
| 2004/0243063 A1 | 12/2004 | Roy et al. |
| 2004/0243156 A1 | 12/2004 | Wu et al. |
| 2005/0038383 A1 | 2/2005 | Kelley et al. |
| 2005/0119678 A1 | 6/2005 | O'Brien et al. |
| 2005/0240148 A1 | 10/2005 | Cheves et al. |
| 2006/0015134 A1 | 1/2006 | Trinidad |
| 2007/0191766 A1 | 8/2007 | McMorrow |
| 2008/0097300 A1 | 4/2008 | Eskaros et al. |

* cited by examiner

*Primary Examiner* — Victoria P Shumate
(74) *Attorney, Agent, or Firm* — Squire Sanders (US) LLP

(57) ABSTRACT

Medical devices for delivering a bioactive agent and methods of use thereof are provided. The device includes a balloon having micro-needles for delivery of the bioactive agent.

16 Claims, 4 Drawing Sheets

Ejected Nano-Beads

Inner Balloon Inflated

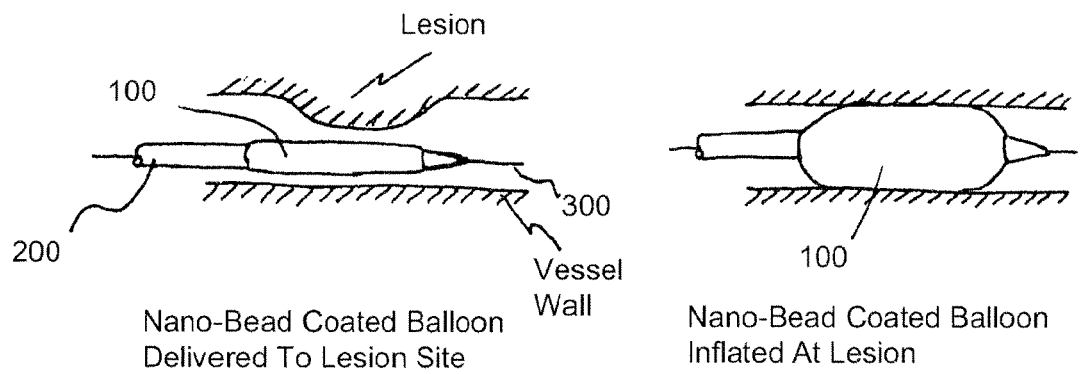
Figure 1A
Figure 1B
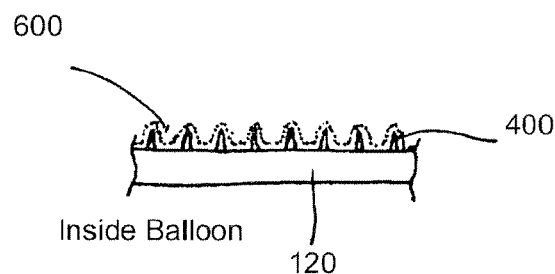
Figure 2
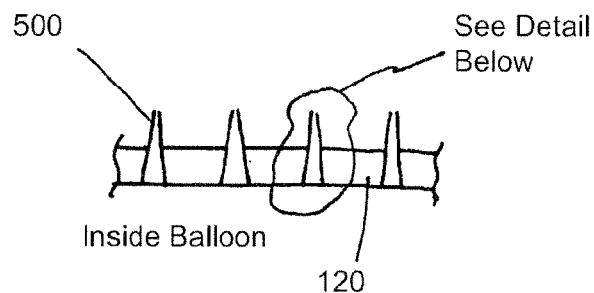
Figure 3A

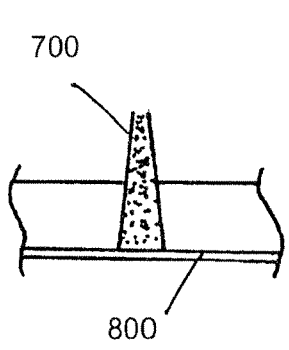
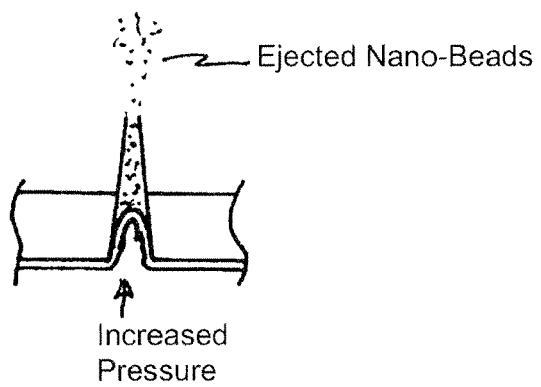
Figure 3B
Figure 3C
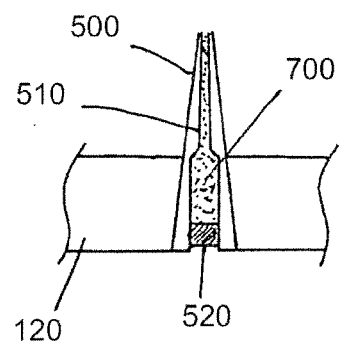
Figure 4
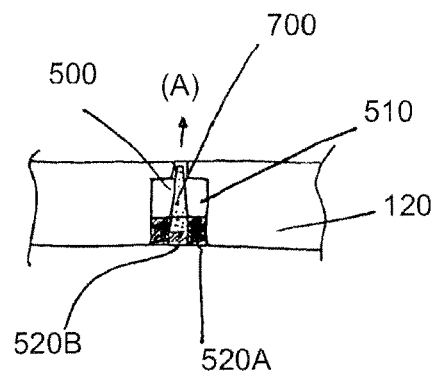
Figure 5

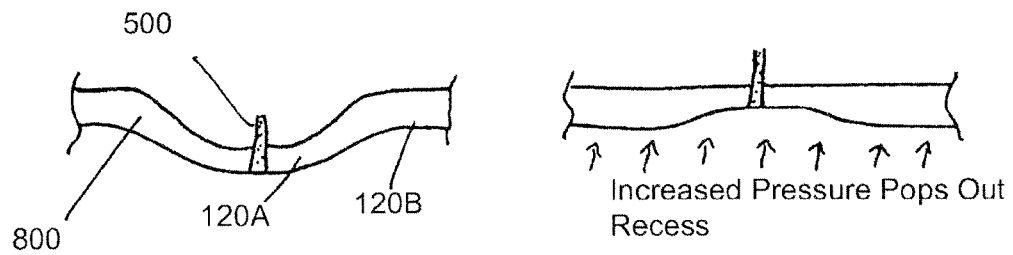
Figure 6A
Figure 6B
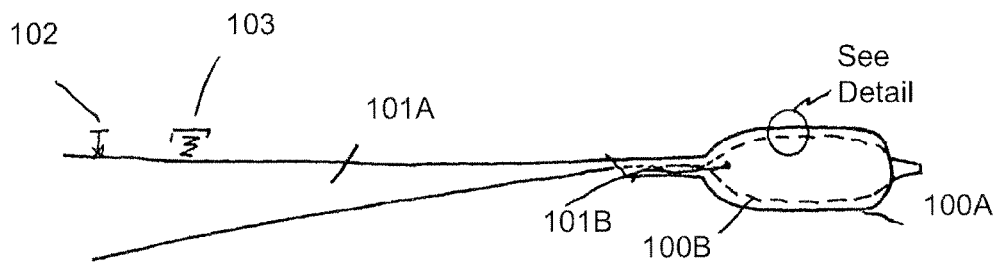
Fluid Circuit Schematic
Figure 7A
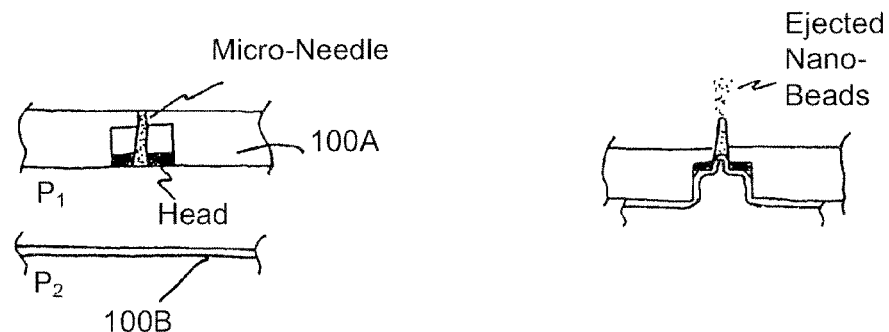
Outer Balloon Inflated
Inner Balloon Inflated
Figure 7B
Figure 7C

DRUG DELIVERY MEDICAL DEVICES

CROSS-REFERENCE

This application is a continuation of application Ser. No. 11/821,998 filed Jun. 25, 2007 and issued as U.S. Pat. No. 8,109,904 on Feb. 7, 2012.

BACKGROUND OF THE INVENTION

1. Field of the Invention

This invention is generally related to drug delivery devices, such as balloons devices for drug delivery.

2. Description of the State of the Art

Drug delivery to the vascular is currently done orally, by direct injection, and drug coated stent. Also most recently, mechanical intervention of vascular conditions is used as a vehicle for providing biological therapy. For example, drug coated balloons have been experimented with. The drug coated stent and balloon have the advantage of delivering the drug directly to the target location. The drug target may be a lesion, restenosed stent, venerable plaque, or other treatable vascular anomaly.

The delivery of these nanobeads, and also the delivery of drugs from conventional drug eluting stents or drug coated balloons, to a lesion are by drug releasing from the nanobeads, or drug coating, through the vessel wall into the lesion and surrounding tissue. During this process the majority of the drug, about 90%, is lost to the blood stream.

Additionally, a problem associated with the balloon as drug delivery vehicle is that it can not be inflated for long, as stopping the blood flow in the vessel is detrimental to the patient.

The embodiments described below address the above-identified problems.

SUMMARY

The present invention provides a medical device for delivery of a bioactive agent(s). The bioactive agent(s) can be included in a composition that may or may not include nanobeads. In some embodiments, the bioactive agent(s) are included or encapsulated in a plurality of nanobeads or pluralities of nanobeads.

The medical device can be a balloon drug delivery device. The balloon device can include a drug delivery mechanism. The mechanism is capable of substantially increasing the transfer of drug to the treatment site. In some embodiments, the drug delivery mechanism comprises microspikes, microneedles or combinations of these. In some embodiments, the mechanism includes microspikes or microneedles coated with a composition including a bioactive agent(s) or microneedles capable of delivering a composition including a bioactive agent(s). In some embodiments, the mechanism includes microneedles capable of delivering a composition including a bioactive agent(s).

In some embodiments, the drug transfer is achieved by ejection of the nanobeads into the vessel wall after the balloon has been inflated against the vessel wall.

In some embodiments, the present invention provides a medical device comprising a balloon and a drug delivery mechanism attached to the balloon. The medical device is in a size suitable for delivering a composition comprising at least one bioactive agent to a vessel in a lesion site of a vascular tissue. The balloon expands in response to pressure as to contact the wall of the vessel to open the vessel.

In some embodiments, the drug delivery mechanism comprises a microstructure selected from microspike, microblade, solid microneedle, hollow microneedle, or combinations thereof. In some embodiments, the drug delivery mechanism can further comprise an ejection mechanism, the microstructure comprises hollow microneedles comprising an inner cavity that is communicable with the balloon through the ejection mechanism, and the ejection mechanism is capable of ejecting the composition into the vascular tissue through the microneedles. The microneedle can comprise an apex and a head. In some embodiments, the apex of the microneedle can be positioned above or beneath the outer surface of the balloon skin.

The term "microblade" refers to a microstructure having a microscale body with a sharp (nanoscale) edge; the term "solid microneedle" refers to a solid microstructure having a microscale body with a nanoscale tip; and the term "microspike" refers to a microstructure having a microscale body with a nanoscale edge or a nanoscale tip. In some embodiments, microspikes and microblades can have a microstructure body in an angle in relation to the plane of the substrate, which, in some embodiments, can be plane of the balloon skin. In some embodiments, the terms "microspike" and "microblade" can be used interchangeably. In some embodiments, the terms "microspike" and "solid microneedle" can be used interchangeably.

As used herein, the term "microneedle" refers to hollow microneedles unless otherwise specified. The term "nanoscale" refers to a size of about 10 nm to about 1000 nm, and the term "microscale" generally refers to a size in the range of about 1 μm to about 500 μm.

The ejection mechanism is responsive to a change of pressure. In some embodiments, the ejection mechanism comprises a flexible membrane positioned between the microneedle and the inner cavity of the balloon. The ejection mechanism can be responsive to an increase of pressure to balloon into the inner cavity of the microneedle to push the microneedle into the wall of vessel in the lesion site and eject the composition into the vascular tissue.

In some embodiments, the ejection mechanism comprises a piston, and the piston is responsive to an increase of pressure to push the microneedle into the wall of the vessel in the lesion site to eject the composition into the vascular tissue.

In some embodiments, the ejection mechanism comprises an outer piston and an inner piston, the outer piston is responsive to an increase of pressure to push the microneedle toward the wall of vessel to expose the microneedle above the outer surface of the balloon skin and push the microneedle into the wall of the vessel in the lesion site, and the inner piston is responsive to a further increase of the pressure to eject the composition into the vascular tissue.

In some embodiments, the balloon in the drug delivery device can comprise thinned skin and normal skin, the microneedles are attached to the thinned skin such that the apex of the microneedle is beneath the outer surface of the balloon skin, the ejection mechanism comprises a flexible membrane positioned between the microneedle and the inner cavity of the balloon, and the thinned skin is responsive to an increase of pressure (P1) to push the microneedle above the outer surface of the balloon skin and into the wall of vessel in the lesion site. The flexible membrane is responsive to an even higher increase in pressure (P2) to balloon into the inner cavity of the microneedle to eject the composition into the vascular tissue.

In some embodiments, the balloon in the drug delivery device can comprise: (a) an outer balloon skin comprising an outer balloon fluid path, a stop cock for closing the outer balloon fluid path and a pressure relief valve for maintaining the pressure of the outer balloon fluid path; and (b) an inner balloon skin comprising an inner balloon fluid path. The microneedle is positioned in the outer balloon skin and beneath the outer surface of the outer balloon skin. The outer balloon skin is responsive to a first pressure (P1) to expand as to contact with the vessel wall to open up the vessel in the lesion site. The inner balloon skin is capable of (a) expansion at P1 to make contact with the head of the microneedle and push the microneedle to protrude outside the outer balloon and (b) ballooning into the inner cavity of the microneedle to push the microneedle into the wall of the vessel in the lesion site at a higher pressure (P2) to eject the composition into the vascular tissue.

In some embodiments, the composition is a coating on the microstructure. In some embodiments, the composition can include a plurality or multiple pluralities of nanobeads. The composition can include a bioactive agent(s).

In some embodiments, the present invention provides a method of treating or ameliorating a medical condition in a lesion site of a vessel in a subject, e.g., a human being. The method includes delivering into a vessel in a lesion site in a vascular tissue of a patient a composition comprising at least one first bioactive agent through the drug delivery device described herein, wherein the medical device provides an initial burst of the at least one first bioactive agent to the site. In some embodiments, the method can further include implanting in the lesion site an implantable device that provides a sustained release of at least one second bioactive agent from the implantable device. The implantable device can be a stent, which can be durable or bioabsorbable. The at least one first bioactive agent and the least one second bioactive agent are the same or different.

The drug delivery device provided herein can include at least the following advantages:

a) most of the drug is transferred to the target site rather than being lost to the blood stream, which causes a systemic effect;

b) systemic effects of the drug are reduced. This is of particular advantage when dealing with potent or toxic drugs for targeted use. These drugs may have detrimental effects to some vital organs;

c) drug dose quantity to the target area is much more controlled. This is due to the greatly reduced amount of drug loss to the blood stream and the control of the injected amount of drug;

d) in some of the designs below, the microneedles or microspikes are recessed for delivery. This prevents microneedle or microspike damage and also vessel damage during delivery; and e) this mechanism would allow for applications where the drug was not encapsulated in nanobeads.

The bioactive agents can be any diagnostic, therapeutic, or prophylactic agent. Some examples of the bioactive agents are paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), TAFA-93, biolimus-7, biolimus-9, clobetasol, pimecrolimus, imatinib mesylate, midostaurin, prodrugs thereof, co-drugs thereof, or combinations thereof.

The medical device described herein can be used to treat, prevent or ameliorate a medical condition in a patient by implanting in the patient the medical device and causing nanobeads in the medical device to release from the medical device so as to release the bioactive agent(s) to treat, prevent, or ameliorate the medical condition. Some examples of medical conditions or disorders that can be treated, prevented, or ameliorated by the medical device described herein include, but are not limited to, atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof.

BRIEF DESCRIPTION OF THE DRAWINGS

FIGS. 1A and 1B illustrate an embodiment of the present invention, which demonstrates nanobead coated balloon operation;

FIG. 2 shows drug nanobeads in slurry coating microspikes on balloon surface;

FIGS. 3A-3C show microneedles with flexible membrane to eject drug nanobeads;

FIG. 4 shows microneedles with piston to eject drug nanobeads;

FIG. 5 shows recessed microneedles with pistons to eject drug nanobeads;

FIGS. 6A-6B show balloon skin dimple recessed microneedles with flexible membrane to eject drug nanobeads;

FIG. 7A-7C show an embodiment of the present invention, which is precision controlled duel skin balloon for exposing and/or injecting from hollow microneedles.

DETAILED DESCRIPTION

Figures 8A, 8B, 8C:
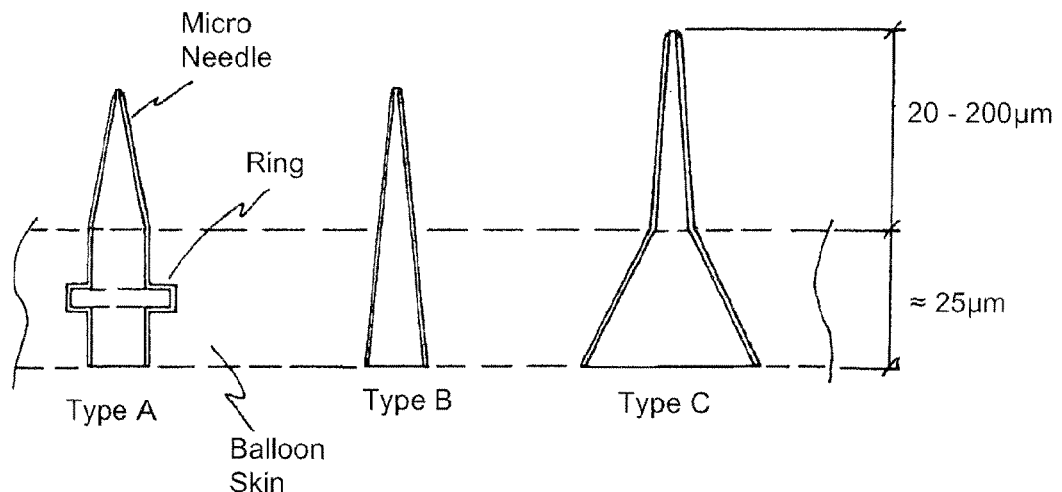
FIGS. 8A-8E show embodiments of the present invention, which are microneedles having different shapes and configurations.

The present invention provides a medical device for delivery of a bioactive agent(s). The bioactive agent(s) can be included in a composition that may or may not include nanobeads. In some embodiments, the bioactive agent(s) are included or encapsulated in a plurality of nanobeads or pluralities of nanobeads.

The medical device can be a balloon drug delivery device. The balloon device can include a drug delivery mechanism. The mechanism is capable of substantially increasing the transfer of drug to the treatment site. In some embodiments, the drug delivery mechanism comprises microspikes, microneedles or combinations of these. In some embodiments, the mechanism includes microspikes, microblades, or microneedles, which can be hollow or solid, coated with a composition including a bioactive agent(s) or microneedles capable of delivering a composition including a bioactive agent(s). In some embodiments, the mechanism includes microneedles capable of delivering a composition including a bioactive agent(s).

In some embodiments, the drug transfer is achieved by ejection of the nanobeads into the vessel wall after the balloon has been inflated against the vessel wall.

In some embodiments, the present invention provides a medical device comprising a balloon and a drug delivery mechanism attached to the balloon. The medical device is of a size suitable for delivering a composition comprising at least one bioactive agent to a vessel in a lesion site of a vascular tissue. The balloon expands in response to pressure as to contact the wall of the vessel to open the vessel.

In some embodiments, the drug delivery mechanism comprises a microstructure selected from microspike, solid microneedle, hollow microneedle, or combinations thereof. In some embodiments, the drug delivery mechanism can further comprise an ejection mechanism, the microstructure comprises hollow microneedles comprising an inner cavity that is communicable with the balloon through the ejection mechanism, and the ejection mechanism is capable of ejecting the composition into the vascular tissue through the microneedles. The microneedle can comprise an apex and a head. In some embodiments, the apex of the microneedle can be positioned above or beneath the outer surface of the balloon skin.

The ejection mechanism is responsive to a change of pressure. In some embodiments, the ejection mechanism comprises a flexible membrane positioned between the microneedle and the inner cavity of the balloon. The ejection mechanism can be responsive to an increase of pressure to balloon into the inner cavity of the microneedle to push the microneedle into the wall of vessel in the lesion site and eject the composition into the vascular tissue.

In some embodiments, the ejection mechanism comprises a piston, and the piston is responsive to an increase of pressure to push the microneedle into the wall of the vessel in the lesion site to eject the composition into the vascular tissue.

In some embodiments, the ejection mechanism comprises an outer piston and an inner piston, the outer piston is responsive to an increase of pressure to push the microneedle toward the wall of vessel to expose the microneedle above the outer surface of the balloon skin and to push the microneedle into the wall of the vessel in the lesion site, and the inner piston is responsive to a further increase of the pressure to eject the composition into the vascular tissue.

In some embodiments, the balloon in the drug delivery device can comprise thinned skin and normal skin, the microneedles are attached to the thinned skin such that the apex of the microneedle is beneath the outer surface of the balloon skin, the ejection mechanism comprises a flexible membrane positioned between the microneedle and the inner cavity of the balloon, and the thinned skin is responsive to an increase of pressure (P1) to push the microneedle above the outer surface of the balloon skin and into the wall of vessel in the lesion site, the flexible membrane is responsive to a further increase of pressure (P2) to balloon into the inner cavity of the microneedle and to eject the composition into the vascular tissue.

In some embodiments, the balloon in the drug delivery device can comprise: (a) an outer balloon skin comprising an outer balloon fluid path, a stop cock for closing the outer balloon fluid path and a pressure relief valve for maintaining the pressure of the outer balloon fluid path; and (b) an inner balloon skin comprising an inner balloon fluid path. The microneedle is positioned in the outer balloon skin and beneath the outer surface of the outer balloon skin. The outer balloon skin is responsive to a first pressure (P1) to expand as to contact with the vessel wall to open up the vessel in the lesion site. The inner balloon skin is capable of (a) expansion at a pressure higher than P1 to make contact with the head of the microneedle and push the microneedle to protrude outside the outer balloon and to push the microneedle into the wall of the vessel in the lesion site (b) ballooning into the inner cavity of the microneedle at a higher pressure (P2) to eject the composition into the vascular tissue. As used herein, the term "higher than P1" can mean slightly higher than P, which can be higher by a factor of e.g., about 0.001%, about 0.01%, about 0.1%, about 1%, about 5%, about 10%, about 20%, etc. In some embodiments, the term "higher than P1" can be by a factor of about 30%, about 40%, about 50% or higher. An ordinary skill in the art can determine a proper "higher than P1" pressure to use.

In some embodiments, the composition is a coating on the microstructure. In some embodiments, the composition can include a plurality or multiple pluralities of nanobeads. The composition can include a bioactive agent(s).

In some embodiments, the present invention provides a method of treating or ameliorating a medical condition in a lesion site of a vessel in a subject, e.g., a human being. The method includes delivering into a vessel in a lesion site in a vascular tissue of a patient a composition comprising at least one first bioactive agent through the drug delivery device described herein, wherein the medical device provides an initial burst of the at least one first bioactive agent to the site. In some embodiments, the method can further include implanting in the lesion site an implantable device that provides a sustained release of at least one second bioactive agent from the implantable device. The implantable device can be a stent, which can be durable or bioabsorbable. The at least one first bioactive agent and the least one second bioactive agent are the same or different.

The drug delivery device provided herein can include at least the following advantages:

a) most of the drug is transferred to the target site rather than being lost to the blood stream, which causes a systemic effect;

b) systemic effects of the drug are reduced. This is of particular advantage when dealing with potent or toxic drugs for targeted use. These drugs may have detrimental effects to some vital organs;

c) drug dose quantity to the target area is much more controlled. This is due to the greatly reduced amount of drug loss to the blood stream and the control of the injected amount of drug;

d) in some of the designs below, the microneedles or microspikes are recessed for delivery. This prevents microneedle or microspike damage and also vessel damage during delivery; and e) this mechanism would allow for applications where the drug was not encapsulated in nanobeads.

The bioactive agents can be any diagnostic, therapeutic, or prophylactic agent. Some examples of the bioactive agents are paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), TAFA-93, biolimus-7, biolimus-9, clobetasol, pimecrolimus, imatinib mesylate, midostaurin, prodrugs thereof, co-drugs thereof, or combinations thereof.

The medical device described herein can be used to treat, prevent or ameliorate a medical condition in a patient by implanting in the patient the medical device and causing nanobeads in the medical device to release from the medical device so as to release the bioactive agent(s) to treat, prevent, or ameliorate the medical condition. Some examples of medical conditions or disorders that can be treated, prevented, or ameliorated by the medical device described herein include, but are not limited to, atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof.

The medical device provided in the present application is also sometimes referred to as a "drug delivery device."

As used herein, the term "balloon" refers to any device capable of expansion with a pressure. In some embodiments, the balloon is formed of a material that comprises an elastic material. In some embodiments, balloons can be made from a semi rigid material or layers of rigid and flexible materials. These materials have the property of expanding to the designed cylindrical diameter and no further even though more pressure is applied to the inside of the balloon. Some examples of balloons can withstand 20 atmospheres of pressure or more. This feature makes them excellent in forcing a lesion, even if heavily calcified, to the desired diameter.

Balloon Devices

The basic principal of the design of the balloon devices provided herein is shown in FIGS. 1A and 1B. FIG. 1A demonstrates that a balloon device 100 coated with nanobeads (not shown) including a bioactive agent is delivered to a lesion site on a blood vessel wall. The balloon can be navigated to the lesion site according to normal vascular intervention procedures. For example, the balloon can be delivered to the lesion site via a catheter 200 and a guidewire 300. The balloon is then inflated to expand the lesion by pushing against the vessel wall (FIG. 1B). Drug encapsulated nanobeads are then transferred to the lesion and/or vessel wall and/or injected into the vessel wall itself. The details of drug delivery via balloon is further explained below.

FIG. 2 shows an embodiment of the balloon device 100, which includes balloon skin or balloon wall 120, microspikes 400, and a coating 600 on the microspikes that includes nanobeads including a drug(s) in a slurry. The balloon 100 can be inflated against the lesion and vessel wall as shown in FIG. 1B. As it expands, the balloon 100 will press against the lesion and vessel wall. The microspikes 400 will penetrate the surface of the lesion and vessel wall. The coating 600 on the balloon surface and microspikes will transfer to the lesion and vessel wall and will also be forced into the holes created by the microspikes.

FIGS. 3A-3C show an embodiment of the present invention, which is a balloon 100 including balloon skin 120 and microneedles 500. FIG. 3A shows microneedles 500 formed on the balloon skin/wall 120 of a balloon 100 (not shown). The microneedles 500 can contain a composition including a bioactive agent(s), such as nanobeads 700 (FIG. 3B). The microneedle cavity and the inner side of balloon is separated by a flexible membrane 800 (FIG. 3B). The balloon is pressurized until the balloon expands (FIG. 3B), makes contact with the lesion and vessel wall, and expands the lesion to the normal vessel diameter. During this process the microneedles 500 can pierce the outer cell layers of the lesion and vessel wall but no drug is delivered. Subsequently, the balloon is further pressurized. At this stage the designed flexible membrane 800 under each microneedle balloons into the microneedle cavity, thus injecting nanobeads 700 or a composition including bioactive agent(s) into the lesion and vessel wall (FIG. 3C).

FIG. 4 shows a further embodiment of the present invention, which is a balloon 100 including balloon skin 120 and microneedles 500. The microneedles 500 have a cylinder wall 510 and a piston 520 separating the inner cavity of the microneedles 500 and the inner cavity of the balloon 100. The microneedles 500 can contain a composition including a bioactive agent(s), such as nanobeads 700. In operation, the balloon 100 is pressurized until the balloon expands, makes contact with the lesion and vessel wall, and expands the lesion to the normal vessel diameter. During this process the microneedles 500 can pierce the outer cell layers of the lesion and vessel wall but no drug is delivered. Subsequently, the balloon 100 is further pressurized. The increased pressure can cause on the piston 520 to overcome the frictional force between the piston and the cylinder wall and the piston moves towards the microneedle apex, ejecting the nanobeads 700 or a composition including bioactive agent(s) into the lesion and vessel wall.

FIG. 5 shows a further embodiment of the present invention, which is a balloon 100 including a balloon skin 120 and microneedles 500. The microneedle 500 has a cylinder wall 510, an outer piston 520A and an inner piston 520B, separating the inner cavity of the microneedles 500 and the inner cavity of the balloon 100. The microneedles 500 can contain a composition including a bioactive agent(s), such as nanobeads 700. In operation, the balloon is pressurized until the balloon expands, makes contact with the lesion and vessel wall. As pressure is increased the balloon expands the lesion to the normal vessel diameter. During this process, the increased pressure acts on the outer piston 520A, forcing it towards the vessel wall (direction A). This exposes the microneedle above the balloon surface and forces it into the lesion and vessel wall. At this stage no nanobeads 700 have been ejected from the microneedles. The balloon is then further pressurized. The increased pressure force on the inner piston 520B moves it towards the microneedle apex, ejecting the nanobeads 700 into the lesion and vessel wall.

FIGS. 6A-6B show a further embodiment of the present invention, which is a balloon 100 including a balloon skin 120 and microneedles 500. The balloon skin 120 includes thinned balloon 120A in the area with and surrounding a microneedle 500 and normal balloon skin 120B in the area without a microneedle. The microneedle cavity and the inner side of balloon is separated by a flexible membrane 800. FIG. 6A shows the deflated state of the balloon 100. In operation, the balloon is pressurized until the balloon expands, makes contact with the vessel wall of a lesion site (FIG. 6B). At this stage the pressure builds up and expands the balloon and opens up the lesion to the normal vessel diameter. At the same time, the increased pressure acting on the balloon dimples forces them to pop outward. This in turn exposes the microneedles and forces them into the lesion and vessel wall. No nanobeads have been injected at this stage. Delivery of the bioactive agent(s) nonetheless can be achieved by using microspikes or microneedles (solid or hollow) coated with a composition nanobeads including the bioactive agent(s), which is described above.

Further to the description of the above operation of the device shown in FIGS. 6A and 6B, the balloon is then further pressurized. At this stage the designed flexible membrane 800 under each microneedle 500 balloons into the microneedle cavity, thus injecting nanobeads into the lesion and vessel wall. Note, the embodiments of the ejection system using a piston described above can also be used here.

Referring to FIGS. 7A-7C, an embodiment of the present invention provides a balloon device 100 that includes an outer balloon (also referred to as outer balloon skin) 100A and an inner balloon (also referred to as inner balloon skin) 100B. The outer and inner balloons 100A and 100B have separate fluid paths, 101A and 101B, from the proximal end of the catheter (FIG. 7A). The outer balloon fluid path 101A is also fitted with stop cock 102 and a pressure relief valve 103.

Referring to FIG. 7B, the outer balloon 100A is first pressurized until the balloon expands, makes contact with the vessel wall. At this stage the pressure builds up and expands the balloon and opens up the lesion to the normal vessel diameter. This pressure is called pressure P1. The operator of the device (e.g., a doctor) can then set the relief valve 103 to just above pressure P1 and closes the stop cock 102. If the pressure increases above P1, the relief valve 103 will open and dump the outer balloon pressurizing fluid until the pressure again reduces to P1.

Referring to FIGS. 7A and 7B, the inner balloon skin 100B is used for precise control of microneedle exposure and nanobead injection timing. When the operator of the device (e.g., a doctor) desires, he/she inflates the flexible inner balloon 100B. As this balloon inflates it will displace the fluid in the outer balloon 100A thus increasing the pressure in this balloon. This will cause the relief valve 103 to open and the pressure to drop to P1.

Referring to FIGS. 7B and 7C, as the inner balloon 100B expands it will make contact with the head of the microneedle and push the microneedle to cause it to protrude outside the outer balloon and penetrate the lesion. A higher pressure is then applied to the inner balloon to eject a precise amount of nanobeads as discussed above in FIGS. 3A-3C.

Still referring to FIGS. 7A-7C, once the procedure has been completed, the inner balloon 100B and outer balloon 100A are deflated and a catheter is extended over the balloon and microneedles for protected withdrawal from the vascular.

In some embodiments, the precision duel skin balloon system as shown in FIGS. 7A-7C can be applied to any of the embodiments described herein.

FIGS. 8A-8E shows a few embodiments of the microneedles of the present invention. FIG. 8A shows a microneedle that could be inserted into a lased hole in the balloon skin. This shape would be suitable for a delivery system as described in FIG. 3A-3C or 4, discussed above.

FIG. 8B shows a microneedle which has a conical shape. This shape would be suitable for a delivery system as shown in FIGS. 3A-3C, discussed above.

FIG. 8C shows a microneedle that has a larger inner opening so the flexible balloon skin of a device as shown in FIG. 3 could deliver more drug.

Figures 8D, 8E:
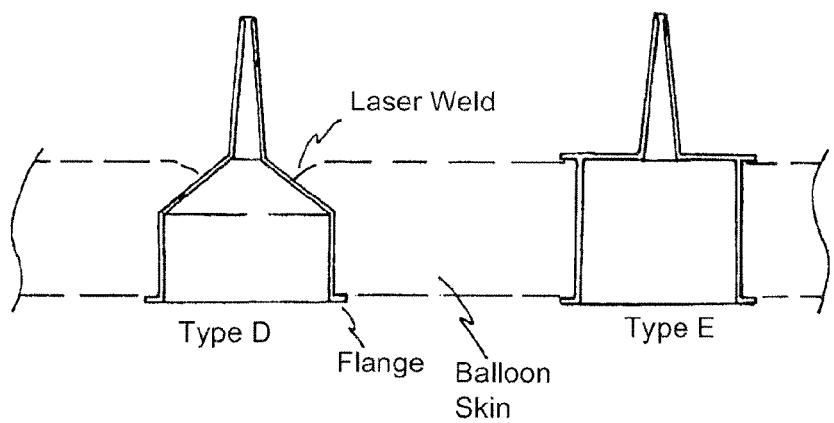

FIGS. 8D and 8E show microneedles having shapes that allow a relatively large drug delivery reservoir for delivery systems as shown in FIGS. 3A-3C and 4. The flanges are options for needle retention.

In some embodiments, microneedles or microspikes can be formed on one side of the balloon only. This embodiment would allow drug treatment to a more precise target area such as a lesion. This can be an advantage when using highly potent or toxic drugs. Balloon orientation would be by radiopaque markers that appear differently at different orientations.

In some embodiments, the balloon device can use different lengths or different combinations of lengths for microneedles or microspikes on a device. This would allow treatment to different vessel wall depths of the treatment site. This would be useful in tailoring different drug distributions for specific tissue types. Further, various microneedles on a device could be filled with different drug nanobeads or composition can be injected to different depths to tailor the treatment of different medication characteristics.

In some embodiments, the various embodiments described herein can include a catheter that can be extended over the balloon and microneedles for protected withdrawal from the vascular.

The microspikes and microneedles on the balloon can have different size. Generally, the microspikes or microneedles can have a size ranging from about 1 µm to about 1000 µm, e.g., about 5 µm, about 10 µm, about 20 µm, about 50 µm, about 75 µm, about 100 µm, about 150 µm, about 200 µm, about 300 µm, or about 500 µm. The size of the cylinder in the microneedle and the piston, including the inner cylinder and outer cylinder, described above, can have a size such that the cylinder and pistons, including the inner and outer cylinders, are operable with the microneedle, which can be readily determined by a person of ordinary skill in the art.

The microstructure, including microneedles, solid microneedles, microspikes, microblades can have various aspect ratio, e.g., a low aspect ratio or a high aspect ratio. In some embodiments, the microstructure can have an aspect ratio of about 5 or above, e.g., about 7, about 10, about 15, about 20, about 25, about 30, about 50, or about 100.

Fabrication

The balloon devices described above can be readily fabricated by established method in the art. A person of ordinary skill in the art can readily fabricate the devices described above according to established methodology in the art. For example, the balloon skin could be etched or molded with microneedle shapes. Then metal would be added by electro deposition to non-masked areas. The holes would need to be laser drilled. Alternatively, especially for larger needles, small molds could be made and electro deposition of metal onto the molds would be conducted. The mold would then be dissolved away leaving the microneedle. This microneedle would then be inserted into the balloon skin and secured by thermal or laser welding. Microneedles could be from 20 to 200 µm in length as shown. Balloons are typically in the order of 25 µm thick. This process would also apply to microspikes, solid microneedles, or microblades. Hard polymers could also be used for needles. In this case the needles would be formed by drawing hollow tubes of polymer and stretching them with heat into cone shapes.

Methods for fabricating both solid and hollow microneedles in a broad range of shapes with feature sizes from one to 1,000 microns have been reported. For example, Prausnitz et al. fabricated microneedle arrays from metal and polymer materials that have sufficient strength to reliably penetrate the skin without breakage.

Methods using molds were also used to fabricate microneedle devices without the need for creating silicon needles to use as masters. Metal microneedles were produced through electrodeposition onto laser-drilled polymer molds, while glass microneedle masters were fabricated using conventional drawn-glass micropipette techniques. Using reactive ion etching microfabrication techniques originally developed for integrated circuits, solid silicon microneedle arrays of about 10 millimeters square were fabricated. The existing needles can vary, some examples of which can be 150 microns long and leave holes about one micron in diameter when removed from the skin.

Attachment of the microneedles or microspikes to the balloon 100 can be achieved by established methods. For example, FIG. 8A shows a microneedle that could be inserted into a lased hole in the balloon skin. To achieve this, the ring area would be heated by a heating element, electrical induction, ultrasonic horn, or laser beam to soften the balloon skin around the ring so that it conformed to the shape of the ring. This would secure and seal the needle insertion. As another example, the microneedle shown in FIG. 8B can be attached to a balloon skin by laser welding of balloon polymer to metal needle.

Some methods of fabricating microneedle or microspike devices are described in U.S. Pat. Nos. 6,334,856; 6,503,231;

6,611,707; and 6,743,211. Some other information on fabrication of micro devices is discussed in Madou, Marc J., Fundamentals of Microfabrication: The Science of Miniaturization, Second Edition (Hardcover), published by CRC, 2002; and Nam-Trung Nguyen, Steve Wereley, Fundamentals and Applications of Microfluidics, Artech House Publishers, 2002. The teachings of references discussed here are incorporated herein in their entirety by reference.

As an example, an embodiment of the balloon device as shown in FIGS. 6A and 6B where the inner surface of the thinned skin is below the surface of the normal balloon skin (dimple) can be readily formed according to the following. This dimple can be made as the balloon is molded, or locally at each site by dimpling with a tool. The microneedle can be molded or etched into the material, electro-deposition of the microneedle and then heat set to the dimple shape. The advantage of this dimpling shape is that it would "pop" to the microneedle extended state. This sudden extending of the needle into the vessel wall would enhance penetration in hard materials such as calcium. This process would also apply to balloon devices with microspikes, solid microneedles, or microblades.

As another example, an embodiment of the device shown in FIGS. 6A and 6B can have the inner surface of the thinned section at the same level as the normal balloon surface. Also the microneedle tip can still be below the outer surface level of the normal thickness balloon. This can have the advantage of allowing the balloon to be folded as is normally done and thus enhance protection of the microneedles. Manufacture in this case can be by heat setting (thinning) or etching locally at each site. In some embodiments, the width of each thinned out section can be varied to give the desired balance of needle protection, activation pressure, and speed of "popping." This process would also apply to balloon devices with microspikes, solid microneedles, or microblades.

Nanobeads

The nanobeads can be discrete nanobeads or can be included in a coating. In some embodiments, the coating can comprise nanobeads embedded in a slurry. The coating provides for a controlled release of a bioactive agent or agents encapsulated in the nanobeads. The slurry can include a polymer or a non-polymer material. In some embodiments, the slurry comprises a material that can be one of ceramic materials, bioglass, polymer, and combinations thereof.

The nanobeads generally have a size in the range from about 1 nm to over 1000 nm, e.g., about 5 nm, about 10 nm, about 20 nm, about 50 nm, about 80 nm, about 90 nm, about 95 nm, about 100 nm, about 200 nm, about 500 nm, about 800 nm, about 900 nm, about 1000 nm or about 1500 nm. In some embodiments, the nanobeads can have a size from about 10 nm to about 1000 nm, from about 20 nm to about 500 nm, or from about 50 nm to about 200 nm.

In some embodiments, the nanobeads can include a first plurality of nanobeads that encapsulate a first bioactive agent and a second plurality of nanobeads that encapsulate a second bioactive agent. The first plurality of nanobeads and the second plurality of nanobeads can be embedded in the same layer of coating or in different layers of coating, e.g., a first layer comprising the first plurality of nanobeads, and a second layer comprising the second plurality of nanobeads. In some embodiments, the nanobeads can comprise a third plurality of nanobeads that encapsulate a third bioactive agent. The first plurality of nanobeads, the second plurality of nanobeads, and third plurality of nanobeads that encapsulate a third bioactive agent can be embedded in the same layer of slurry coating or in different layers of slurry coating, e.g., a first layer comprising the first plurality of nanobeads, a second layer comprising the second plurality of nanobeads, and a third layer comprising the third bioactive agent. In some embodiments, the first bioactive agent and the second bioactive agent are the same or different. In some embodiments, the first bioactive agent, the second bioactive agent, and the third bioactive agent are the same or different.

In some embodiments, the nanobeads can include more than three pluralities of nanobeads incorporating more than three bioactive agents included in more than three different layers, the first layer including the first plurality of nanobeads, the second layer including the second plurality of nanobeads, the third layer including the third plurality of nanobeads, the fourth layer including the fourth plurality of nanobeads, etc. These agents can be the same or different.

The bioactive agents can be any diagnostic, therapeutic, or prophylactic agent. Some examples of the bioactive agents are paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), clobetasol, pimecrolimus, imatinib mesylate, midostaurin, prodrugs thereof, co-drugs thereof, or combinations thereof.

The medical device described herein can be used to treat, prevent or ameliorate a medical condition in a patient by implanting in the patient the medical device and causing nanobeads in the medical device to release from the medical device so as to release the bioactive agent(s) to treat, prevent, or ameliorate the medical condition. Some examples of medical conditions or disorders that can be treated, prevented, or ameliorated by the medical device described herein include, but are not limited to, atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof.

As used herein, the term "nanoparticles" and "nanobeads" can be used interchangeably. The term "nanocapsules" refers to nanoparticles having a shell encapsulating a bioactive agent. The term "matrix nanoparticles" refers to nanoparticles that do not have a shell where a bioactive agent(s) is dispersed in the matrix of the nanoparticles.

The coating provides for controlled release of the drug(s) through use of different physical and chemical features of the encapsulating matrix or membrane. Once a medical device to which the nanoparticles are coated onto is deployed, the membrane of nanobeads encapsulating a bioactive agent can open up, releasing the drug(s) at controlled intervals and/or levels. Use of different physical and chemical features of the encapsulating membrane(s)/macromolecules/polymers/gels (e.g., microscopic spheres) and drug(s) (e.g., varying-thickness nanoencapsulating membranes, nanoencapsulating membranes of different chemical or physical character, or some combination of these features) leads to modulation of release profile of the bioactive agent in the nanobeads.

The nanobeads can provide a variety of delivery profiles of a bioactive agent. For instance, in some embodiments, the nanobeads can have a layered construct including different layers of spheres such that the outermost spheres have the least (or most) thick membranes (or their equivalent in terms of physical or chemical character) and the innermost spheres might have the greatest (or least) membrane thickness (or equivalent), with intermediate layers such that the overall effect is to provide for a controlled or graduated release of a drug or drugs in terms of time and intensity of the drug and different drugs with different properties (chemical physical and biological) in nanobeads of each layer to target different layers of arterial tissue.

In some embodiments, an initial burst release of drug(s) from nanobeads can be caused by the pressure onto the nanobeads, e.g., pressure from a stent or a balloon delivery device, with a more graduated response to follow that is not pressure dependent.

In some embodiments, the nanobeads described herein can be used in lieu of or in combination with available coating systems for drug delivery stents. In some embodiments, the nanobeads can be used as non-stent delivery systems.

To facilitate the release of nanobeads from the vessel wall, in some embodiments, a patient can ingest or have delivered into the bloodstream a small molecule drug, chemical agent or catalyst to activate/facilitate release of a drug or biopharmaceuticals that are in nanobeads, thus allowing the physician to externally control and very the rate of delivery from the nanobeads of the drug or biopharmaceuticals into the vessel wall. The doctor will thus be able to change the rate of release based upon the evolving assessment of the patient. The mechanism for activating the nanobeads contents could be by allowing the external agent to react with the slurry, the nonobead material or the nonobead contents in such a way that the properties were changed to allow the drug to release. In another embodiment the oral or blood stream delivered drug or other substance would itself have a therapeutic effect. In still another embodiment the oral or blood stream delivered drug or other substance together with the nonobead contents would provide a therapeutic effect different than the individual effect of each alone. In this way the combined effect could provide a much broader and varied therapy. Such small molecule drug, chemical agent or catalyst can be anything that facilitates the release of nanobeads from a module including such nanobeads. For example, a small molecule drug, chemical agent or catalyst can be membrane disruptive or can change the acidity/basicity or enzyme activity surrounding the module. Administration of the small molecule drug, chemical agent or catalyst can therefore cause the nanobeads to be released from the module in the vessel wall.

In some embodiments, a magnetic material(s) (compound or element) can be included in nanobeads. This can allow an electromagnetic source located external to the vascular system to provide for the release of these nanobeads and to direct where they concentrate in the vascular system. Magnetic materials can be any biocompatible magnetic material. Some examples are materials containing iron, platinum elements or compounds. In some embodiments, magnetic materials can be made biocompatible by using a biocompatible coating (e.g., a coating formed of a biocompatible polymeric or nonpolymeric material).

Methods of Forming Nanobead Delivery Systems

In some embodiments, to effect a sustained delivery of the nanobeads, the nanobeads containing a drug can be chemically bonded to a drug delivery system. In some embodiments, the nanobeads can be embedded in a slurry. Such slurry can be, e.g., a biodurable, biodegradable or bioabsorbable material, such as polymer, ceramic, or bioglass.

In some embodiments, chemically attaching the nanobeads to the delivery system can be achieved by coupling the functional groups on the surface of nanobeads and the delivery system. In some embodiments, chemically attaching the nanobeads to the delivery system can be achieved by grafting, e.g., by causing groups on the surface of the nanobeads to bind to the surface of the delivery system. In some embodiments, chemically attaching the nanobeads to the delivery system can be achieved by modification of surface of the nanobeads or the delivery system by attaching silane or siloxane groups to the surface of the nanobeads or the delivery system and then causing the nanobeads to be attached to delivery system via the silane or siloxane groups. The attaching methods are well established in the art (see, e.g., Greg T. Hermanson, "Bioconjugate Techniques", Academic Pree, Elsevier, 1996; J. Biomed. Mater. Res., 60, 472; Langmuer, 18 (2002) 4090; Appl. Polym. Sci., 22,643-664; Macromolecules 34, 7236; J. Ame. Chem. Soc. (2003), 125, 1788; J. Biomed. Mater. Res. (2003), 65A, 196; Macromolecules 26, 5698; Advanced Drug Delivery Reviews, 43, (2002) 3-12, 457-458; J. Polymer Sci. A, Polymer Chem, 28, 219 (1990); Nature, 378, 472 (1995); Nature 411, 59 (2001); Bioconj Chem. 14, 517 (2003); Trans Amer. Soc. Artif Inst Organs, 18, 10 (1972); U.S. Pat. No. 4,424,311; J, Adhes. Sci. Technol. 7, 1065-1076 (1993); Biomaterial 23 (2002) 2043-2056; J. Ame. Chem. Soc., Vol 115, No. 23m 1993, 10715; J Polymer Sci., Symposium No. 51, 135-153 (1975); Angew. Chem., Int. Ed., 2006, 45, 2-20; Anticancer drugs, 16, 243-254; J. Contr. Res., 61, 137 (1999); Macromol Symposia, 172, 49 (2001); Biomaterial, 24, 4495 (2003); Macromoecules (2001) 34, 8657; Macromol Biosci (2004) 4, 192.)

Nanobeads can be readily formed according to methods established in the art. Some examples of forming nanobeads are described in Seshadri and Sivasubramanian, Drug Delivery Technology, 7(3):39-46 (2007). Some other methods are described in the references described above.

Biocompatible Polymers

Any biocompatible polymers can be included in the nanobeads described above and/or a coating including the nanobeads. The biocompatible polymer can be biodegradable (either bioerodable or bioabsorbable or both) or nondegradable, and can be hydrophilic or hydrophobic.

Representative biocompatible polymers include, but are not limited to, poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly (ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(etheresters) (e.g. poly(ethylene oxide-co-lactic acid) (PEO/PLA)), polyalkylene oxides such as poly(ethylene oxide), poly(propylene oxide), poly(ether ester), polyalkylene oxalates, phosphoryl choline, choline, poly(aspirin), polymers and co-polymers of hydroxyl bearing monomers such as 2-hydroxyethyl methacrylate (HEMA), hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as collagen, chitosan, alginate, fibrin, fibrinogen, cellulose, starch, dextran, dextrin, hyaluronic acid, fragments and derivatives of hyaluronic acid, heparin, fragments and derivatives of heparin, glycosamino glycan (GAG), GAG derivatives, polysaccharide, elastin, or combinations thereof. In some embodiments, the nanoparticles can exclude any one of the aforementioned polymers.

As used herein, the terms poly(D,L-lactide), poly(L-lactide), poly(D,L-lactide-co-glycolide), and poly(L-lactide-co-glycolide) can be used interchangeably with the terms poly (D,L-lactic acid), poly(L-lactic acid), poly(D,L-lactic acid-co-glycolic acid), or poly(L-lactic acid-co-glycolic acid), respectively.

In some embodiments, the nanobeads described herein or a slurry including the nanobeads can further include a biobeneficial material. The biobeneficial material can be a polymeric material or non-polymeric material. The biobeneficial material is preferably non-toxic, non-antigenic and non-immunogenic. A biobeneficial material is one which enhances the biocompatibility of the particles or device by being non-fouling, hemocompatible, actively non-thrombogenic, or anti-inflammatory, all without depending on the release of a pharmaceutically active agent.

Bioactive Agents

The bioactive agents encapsulated in the nanobeads described herein can be any bioactive agent, which is a therapeutic, prophylactic, or diagnostic agent. These agents can have anti-proliferative or anti-inflammatory properties or can have other properties such as antineoplastic, antiplatelet, anti-coagulant, anti-fibrin, antithrombonic, antimitotic, antibiotic, antiallergic, and antioxidant. The agents can be cystostatic agents, agents that promote the healing of the endothelium such as NO releasing or generating agents, agents that attract endothelial progenitor cells, or agents that promote the attachment, migration and proliferation of endothelial cells (e.g., natriuretic peptide such as CNP, ANP or BNP peptide or an RGD or cRGD peptide), while quenching smooth muscle cell proliferation. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Some other examples of the bioactive agent include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of antiproliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include 40-epi-(N1-tetrazolyl)-rapamycin (ABT-578), 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anti-coagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, or combinations thereof. Examples of cytostatic substances include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, pimecrolimus, imatinib mesylate, midostaurin, bioactive RGD, and genetically engineered endothelial cells. The foregoing substances can also be used in the form of prodrugs or co-drugs thereof. The foregoing substances also include metabolites thereof and/or prodrugs of the metabolites. The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient, the nature of the trauma, the nature of the therapy desired, the time over which the ingredient administered resides at the vascular site, and if other active agents are employed, the nature and type of the substance or combination of substances.

In some embodiments, the dose will be tailored to the specific anatomy for treatment. Some of these areas are arteries of coronary, cerebral, carotid, renal, iliac, popliteal, tibial, etc. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art. In addition patient state of health, diabetes type of anatomy, type of lesion, severity of lesion and other indicators can be used to determine dose and elution profile.

The bioactive agents described herein can have different release profiles, e.g., fast release (e.g., release of about 50% of the agent within 24 hours), sustained release (e.g., release of about 50% of the agent over a period of days or months), or pulse release profile. In some embodiments, the sustained release profile can be a zero order release.

Method of Use

In accordance with embodiments of the invention, the medical device described herein can be used to deliver any desirable medication or agents to a blood vessel. Generally, the method of use includes delivering a balloon device comprising a drug delivery mechanism described herein having a composition of a drug (e.g., a coating or a discrete composition) to a lesion site in a vascular tissue of a subject (e.g., a human being or patient), causing the balloon to expand as to contact with the wall of vessel in the lesion site, causing the microstructure in the drug delivery mechanism to push or piece or slice into the wall of vessel in the lesion site, and causing the composition to be delivered to the wall of vessel in the lesion site. Exemplary embodiments of this general method are described above.

In some embodiments, the medical device can be used in conjunction with an implantable device. In some embodiments, the implantable device is a stent. The stent described herein is useful for a variety of medical procedures, including, by way of example, treatment of obstructions caused by tumors in bile ducts, esophagus, trachea/bronchi and other biological passageways. A stent having the above-described coating is particularly useful for treating diseased regions of blood vessels caused by lipid deposition, monocyte or macrophage infiltration, or dysfunctional endothelium or a combination thereof, or occluded regions of blood vessels caused by abnormal or inappropriate migration and proliferation of smooth muscle cells, thrombosis, and restenosis. Stents may be placed in a wide array of blood vessels, both arteries and veins.

Representative examples of sites include the iliac, renal, carotid and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described features may then be mechanically expanded or released to self expand at the desired area of treatment. A post-insertion angiogram may also be utilized to confirm appropriate positioning.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

I claim:

1. A medical device, comprising:
   a catheter;
   a balloon disposed at an end of the catheter, the balloon having a first balloon membrane and a second balloon membrane; and
   micro-needles disposed in the first balloon membrane, wherein the micro-needles include a hollow area in which a drug can reside, wherein the second balloon membrane is configured to push the drug out of the hollow area of the micro-needles for application of the drug to a tissue where the balloon has been positioned and expanded, and wherein peaks of the micro-needles reside within the first balloon membrane such that an application of a pressure by the second balloon membrane causes the peaks of the micro-needles to extend out of the first balloon membrane.

2. A medical device, comprising:
   a catheter;
   a balloon disposed at an end of the catheter, the balloon having a first balloon membrane and a second balloon membrane; and
   micro-needles disposed in the first balloon membrane, wherein the micro-needles include a hollow area in which a drug can reside, wherein the second balloon membrane is configured to push the drug out of the hollow area of the micro-needles for application of the drug to a tissue where the balloon has been positioned and expanded, and wherein peaks of the micro-needles reside within the first balloon membrane and are configured to extend out from the first balloon membrane for injection of the drug to the tissue.

3. A medical device, comprising:
   a catheter;
   a balloon disposed at an end of the catheter, the balloon having a balloon membrane; and
   micro-needles disposed in the balloon membrane, such that in a rest state, peaks of the micro-needles reside beneath an outer surface of the balloon membrane, and in an active state the peaks of the micro-needles protrude out from the outer surface of the balloon membrane to deliver a drug to a vessel wall.

4. The device of claim 3, additionally comprising means for causing the peaks of the micro-needles to protrude out from the outer surface of the balloon membrane.

5. The device of claim 4, wherein the means comprises a second balloon membrane configured to push against an end of the micro-needles to cause the peaks of the micro-needles to protrude out from the outer surface of the balloon membrane.

6. The device of claim 3, wherein the micro-needles include an interior reservoir for allowing the drug to be transported to the vessel wall.

7. The device of claim 6, additionally including a means to transport the drug out from the micro-needles to the vessel wall.

8. The device of claim 7, wherein the means to transport the drug comprises a piston-type device configured to push the drug out from the interior reservoir.

9. The device of claim 3, additionally comprising an ejection mechanism that is responsive to a certain pressure applied to the balloon for pushing the micro-needles into the vessel wall such that the drug can be delivered.

10. The device of claim 9, wherein the ejection mechanism is positioned between ends of the micro-needles and an inner cavity of the balloon.

11. The device of claim 3, additionally comprising an ejection mechanism including an inner piston and an outer piston, the outer piston operates to push the micro-needles towards the vessel wall and the inner piston operates to deliver the drug to the vessel wall.

12. The device of claim 3, wherein the balloon further comprises a second balloon membrane, the balloon membrane is in fluid communication with a first fluid path for expansion of the balloon membrane and the second balloon membrane is in fluid communication with a second fluid path, separate from the first fluid path, for expansion of the second balloon membrane to push the micro-needles into the vessel wall for delivery of the drug.

13. The device of claim 12, wherein the first fluid path is operably controlled by a stop cock and a relief valve for maintaining a pressure of a fluid against the balloon membrane.

14. The device of claim 3, wherein the balloon further comprises a second balloon membrane, the balloon membrane is capable of expanding at a first balloon pressure to open the vessel wall and the second balloon membrane is capable of expanding at a greater than first balloon pressure to push the micro-needles out from the balloon membrane.

15. The device of claim 3, wherein the balloon further comprises a second balloon membrane, the balloon membrane is capable of expanding at a first balloon pressure to open the vessel wall and the second balloon membrane is capable of expanding at a greater than first balloon pressure to penetrate into an end of the micro-needles to eject the drug out from the micro-needles.

16. The device of claim 3, wherein the outer surface of the balloon membrane includes a coating including the drug.

* * * * *